United States Patent
Govea et al.

(10) Patent No.: US 9,289,600 B2
(45) Date of Patent: Mar. 22, 2016

(54) ELECTRICAL STIMULATION PADDLE LEADS AND METHODS OF MAKING AND USING

(71) Applicant: BOSTON SCIENTIFIC NEUROMODULATION CORPORATION, Valencia, CA (US)

(72) Inventors: Michael Govea, Glendale, CA (US); Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/091,036

(22) Filed: Nov. 26, 2013

(65) Prior Publication Data

US 2014/0155968 A1    Jun. 5, 2014

Related U.S. Application Data (60) Provisional application No. 61/732,791, filed on Dec. 3, 2012.

(51) Int. Cl.
A61N 1/00 (2006.01)
A61N 1/05 (2006.01)

(52) U.S. Cl.
CPC ......... *A61N 1/0553* (2013.01); *Y10T 29/49117* (2015.01)

(58) Field of Classification Search
CPC .. A61N 1/0551; A61N 1/0553; A61N 1/3605
USPC ........................... 607/117, 116, 115
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2003/0204228 A1* | 10/2003 | Cross et al. ............ 607/116 |
| 2007/0150036 A1 | 6/2007 | Anderson |
| 2010/0325869 A1* | 12/2010 | Skubitz et al. ......... 29/592.1 |
| 2011/0004207 A1* | 1/2011 | Wallace et al. ........... 606/35 |

* cited by examiner

*Primary Examiner* — Christopher D Koharski
*Assistant Examiner* — Philip C Edwards
(74) *Attorney, Agent, or Firm* — Lowe Graham Jones PLLC; Bruce E. Black (57) ABSTRACT

An electrical stimulation lead includes a paddle body, at least one lead body having a distal end, a proximal end, and a longitudinal length with the distal end of the lead body coupled to the paddle body. The lead further includes fixation elements and electrodes. The fixation elements are disposed entirely within the paddle body and the electrodes are disposed on the paddle body. Each of the electrodes includes a stimulating element with an exposed stimulation surface, and a piercing element extending from the stimulating element into the paddle body and making contact with at least one of the fixation elements. Further, the lead includes terminals disposed along the proximal end of the lead body and conductor wires electrically coupling the electrodes to the terminals. In addition, methods of making stimulation leads using sacrificial portions of electrodes are presented.

20 Claims, 9 Drawing Sheets

ELECTRICAL STIMULATION PADDLE LEADS AND METHODS OF MAKING AND USING

CROSS-REFERENCE TO RELATED APPLICATIONS

This application claims the benefit under 35 U.S.C. §119 (e) of U.S. Provisional Patent Application Ser. No. 61/732,791 filed Dec. 3, 2012, which is incorporated herein by reference.

FIELD

The present invention is directed to the area of implantable electrical stimulation systems and methods of making and using the systems. The present invention is also directed towards implantable electrical stimulation leads having electrodes pressed within a lead body, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, for e.g., paddle lead, and an array of stimulator electrodes on each lead. The stimulator electrodes are usually embedded within a non-conductive portion, i.e., a substrate, of the lead.

BRIEF SUMMARY

One embodiment is an electrical stimulation lead that includes a paddle body, at least one lead body having a distal end, a proximal end, and a longitudinal length with the distal end of the lead body coupled to the paddle body. The lead further includes fixation elements and electrodes. The fixation elements are disposed entirely within the paddle body and the electrodes are disposed on the paddle body. Each of the electrodes includes a stimulating element with an exposed stimulation surface, and a piercing element extending from the stimulating element into the paddle body and making contact with at least one of the fixation elements. Further, the lead includes terminals disposed along the proximal end of the lead body and conductor wires electrically coupling the electrodes to the terminals.

In another embodiment, a method of making an electrical stimulation lead includes pressing electrodes into a first portion of a paddle body that is disposed on a base. Each of the electrodes includes a stimulating portion having a stimulating surface that is exposed when the lead is completed and a plurality of legs extending from the stimulating portion and configured and arranged to be pressed into the first portion of the paddle body. A distal portion of each of the legs engages with the base to bend the distal portion at least partially back into the first portion of the paddle body. A conductor wires are coupled to the electrodes. A second portion of the paddle body is formed at least partially beneath the first portion of the paddle body leaving the stimulating surfaces of the electrodes exposed and covering the legs of the electrodes and a portion of each of the conductor wires adjacent the electrodes.

In yet another embodiment, a method of making an electrical stimulation lead includes disposing electrodes in a mold, each of the electrodes including a stimulating portion having a stimulating surface that is exposed when the lead is completed, at least one leg portion extending from the stimulating portion opposite the stimulating surface, and at least one sacrificial portion disposed around the periphery of the stimulating surface and extending from the stimulating surface in a direction opposite the at least one leg portion. The at least one sacrificial portion of each electrode is disposed against a surface of the mold. Conductor wires are coupled to the electrodes and a paddle body is molded around the leg portions of the electrodes and portions of the conductor wires adjacent the electrodes. The at least one sacrificial portion disposed against the mold resists flowing of material from the first portion of the paddle body over the stimulating surfaces of the electrodes. The sacrificial portions of the electrodes are then removed.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed towards implantable electrical stimulation leads having electrodes pressed within a lead body, as well as methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
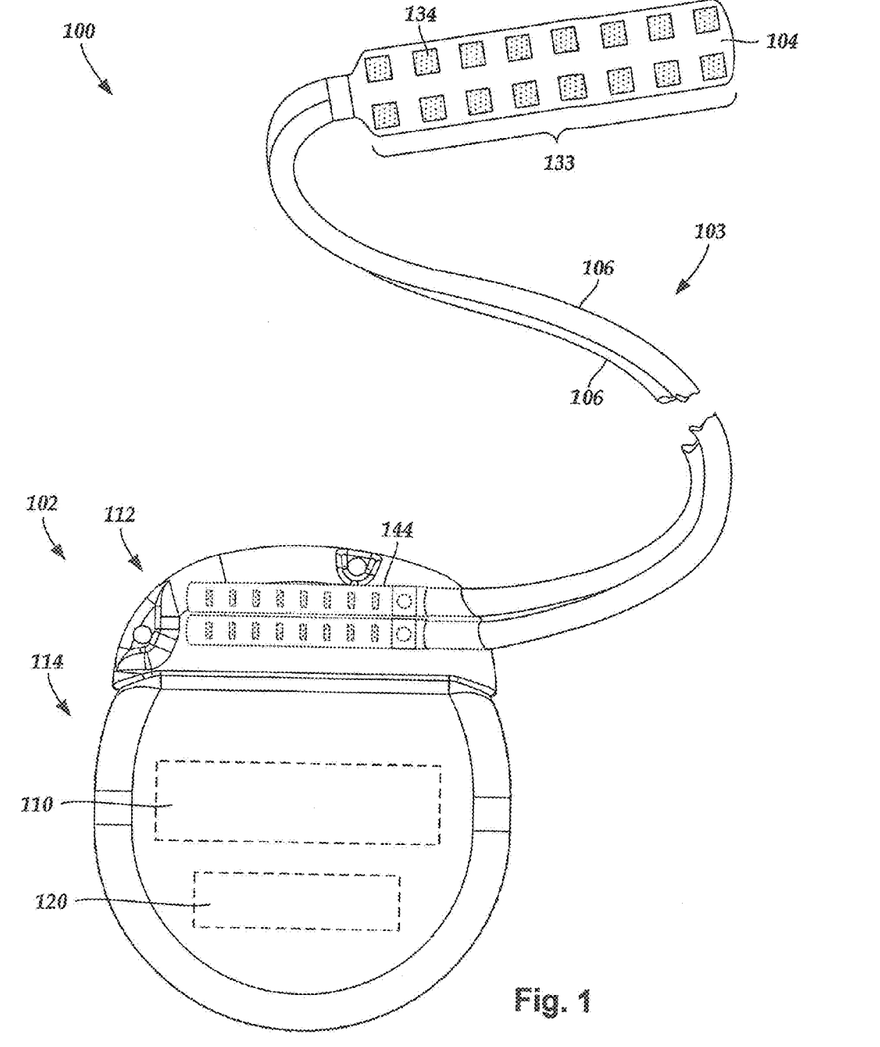
FIG. 1 is a schematic side view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices. For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the paddle body including, for example, four, five, six, seven, eight, nine, ten, eleven, twelve, fourteen, sixteen, twenty-four, thirty-two, or more electrodes 134. The electrodes 134 can be disposed on the paddle body 104 in any suitable arrangement. In FIG. 1, the electrodes 134 are arranged into two columns, where each column has eight electrodes 134.

The electrodes of the paddle body 104 are typically disposed in, or separated by, a non-conductive, biocompatible material such as, for example, silicone, polyurethane, polyetheretherketone ("PEEK"), epoxy, and the like or combinations thereof. The paddle body 104 and the one or more lead bodies 106 may be formed in the desired shape by any process including, for example, molding (including injection molding), casting, and the like. The non-conductive material typically extends from the paddle body 104 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Figure 2A:
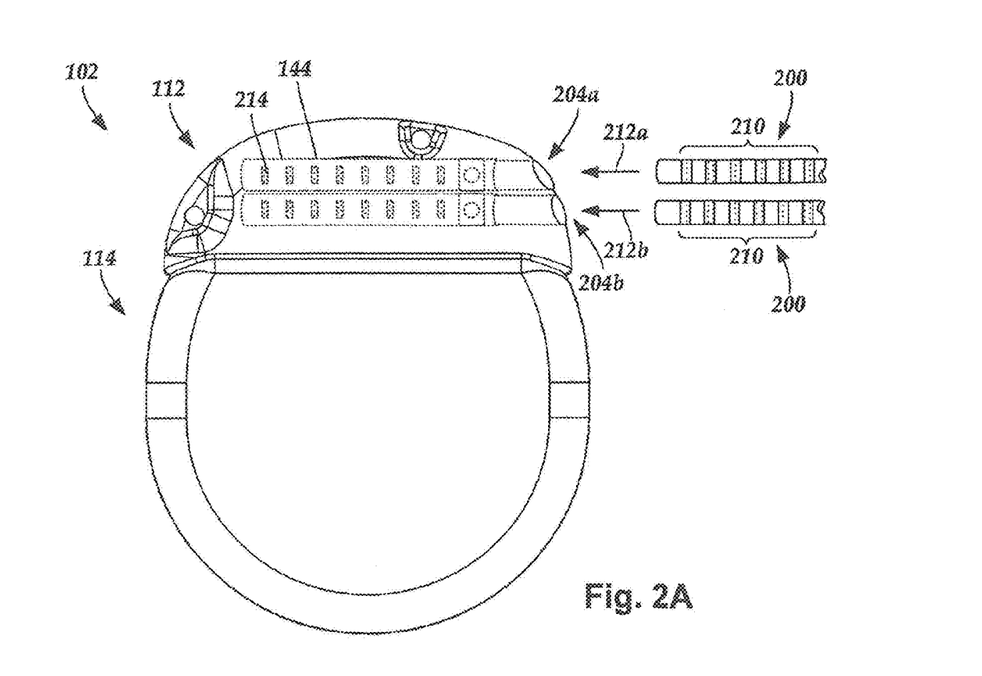
FIG. 2A is a schematic side view of one embodiment of the control module of FIG. 1 configured and arranged to electrically couple to an elongated device, according to the invention.
Figure 2B:
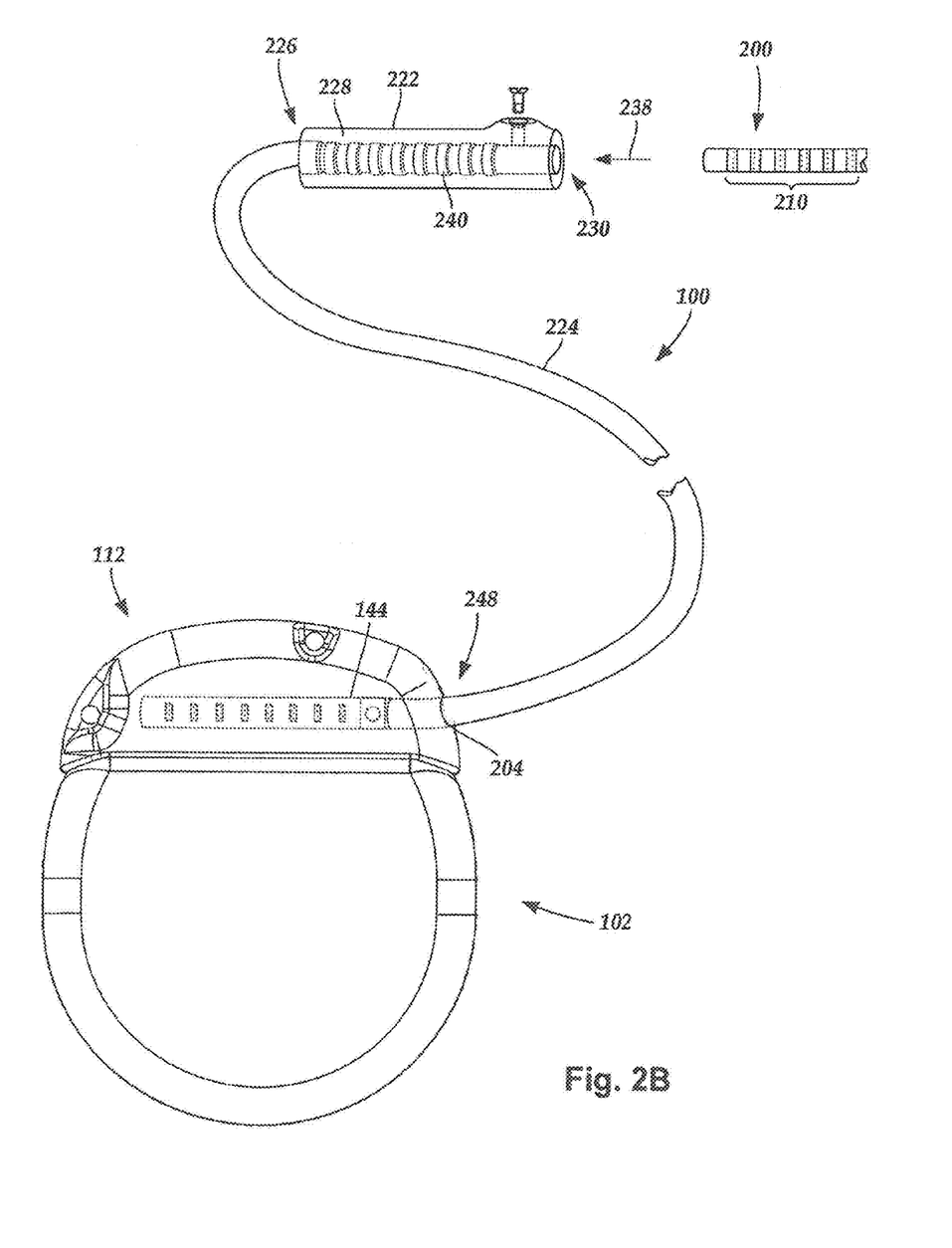
FIG. 2B is a schematic side view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B). The connector contacts are disposed in connectors (e.g., 144 in FIGS. 1-2B; and 222 FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may also be one or more lumens (not shown) that open at, or near, the distal end of the one or more lead bodies 106, for example, for infusion of drugs or medication into the site of implantation of the one or more lead bodies 106. In at least one embodiment, the one or more lumens may be flushed continually, or on a regular basis, with saline, epidural fluid, or the like. In at least some embodiments, the one or more lumens can be permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, one or more of the lead bodies 106 of FIG. 1, one or more intermediate devices (e.g., a splitter, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., one of the lead bodies 106 of FIG. 1, a splitter, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144 (e.g., the ports 204a and 204b of FIG. 1), or to receive multiple elongated devices 200 (e.g., both of the lead bodies 106 of FIG. 1), or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

During manufacture of a paddle lead, the electrodes often placed face-down in the paddle mold (with the stimulating surface of the electrode against the mold) and then molding material is injected into the mold. Some of the molding material may seep between the stimulating surface and the mold. When the paddle is removed from the mold, a portion of the stimulating surface of one or more of the electrodes is covered with a thin layer of the hardened molding material. This material may be referred to as "flash". The flash may reduce the efficacy and stimulating area of the electrodes and, therefore, it is typically desirable to remove the flash from the stimulating surface of each of the electrodes. More preferably, however, is to identify manufacturing techniques that can reduce or prevent the generation of flash on the stimulating surfaces of the electrodes.

FIGS. 3A-3D illustrate one embodiment of a method for forming a paddle portion of a paddle lead. These Figures illustrate the insertion of a single electrodes into the paddle, but it will be understood that the paddle with include multiple electrodes each inserted in the same or similar manner. FIG.

Figure 3A:
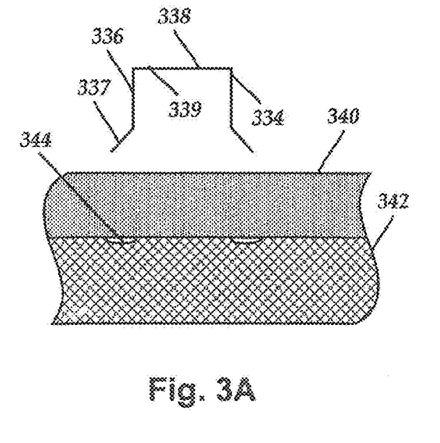
FIG. 3A is a schematic cross-sectional view of one embodiment of an electrode and a first portion of a paddle body, according to the invention.

3A illustrates an electrode 334 and a first portion 340 of a paddle body that is disposed on a base 342. The electrode 334 includes a stimulating portion 338 and one or more legs 336. The stimulating portion 338 includes a stimulating surface, which may be exposed to the ambient surrounding when the lead 106 is complete. The legs 336 extend from the stimulating portion 338 and will be embedded within the first portion 340 of the paddle body. Optionally, the distal portion 337 of the legs 336 may extend at an angle relative to rest of the legs 336. This may facilitate the bending of the distal portion 337 of the legs as described below. FIG. 3A is a cross-sectional view and illustrates two legs. It will be recognized, however, that the electrode may have more than two legs distributed around the circumference of the electrode. Moreover, in some embodiments, a single leg may be provided around the circumference of the electrode with the distal end 337 in FIG. 3A simply representing two sections of that single leg.

The first portion 340 of the paddle body can be made of the any of the materials described above for use with paddle bodies including, but not limited to, silicone or polyurethane. The first portion 340 of the paddle body is sufficiently thin that the legs 336 of the electrode 334 can be pushed entirely through the first portion 340 leaving the stimulating portion 338 exposed on the other side.

A wide variety of materials may be used to form the base 342 including metals, hard polymers, metal-polymer composites, and the like. The base 342 may include one or more indentations 344 in the upper surface of the base 342. These indentations 344 may be adapted in a variety of configurations, i.e., the indentations 344, may be substantially curved or cup-shaped, for receiving portions of the electrode 334. During the first stage of a lead forming process, i.e., the molding stage, the base 342 may be attached to the first portion 340 of paddle body such that the indentations 344 create a gap at an interfacing boundary of the base 342 and the first portion 340 of the paddle body. As an example, the base 342 formed similar to a plate on a desk-top stapler that receives, and bends the distal ends, of the staple.

Figure 3B:
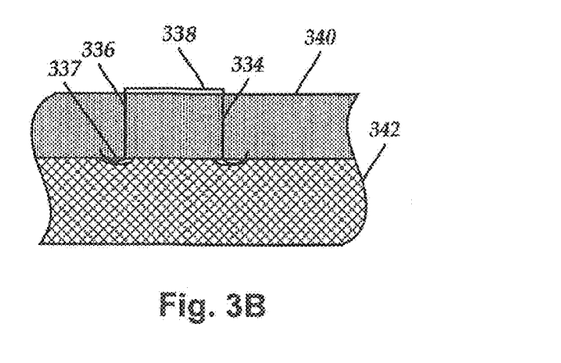
FIG. 3B is a schematic cross-section view of the embodiment of FIG. 3A in which the electrode has been pressed into the first portion of the paddle body, according to the invention.

The electrode 334 is pressed into the first portion 340 of the paddle body as illustrated in FIG. 3B. The electrode 334 may be pressed within the first portion 340 of the paddle body by applying a mechanical force on, for example, the stimulation portion 338 of the electrode 334. The applied force may also push the electrode 334 into contact with the base 342 and bend the distal ends 337 of the legs 336 of the electrode back into the first portion 340 of the paddle body. The indentations 344 in the base 342, if present, as well as the angle at which the distal ends 377 are bend relative to the legs 366, may guide the direction that the distal ends 377 bend. In at least some embodiments, the distal ends 337 of the legs 336 engage with the indentations 344 in the base 342 and then bend outwards. It will be recognized that the distal ends of the legs could also be directed inwards. The distal ends 337 of the legs 336 bend back to at least partially pierce the first portion 340 of the paddle body. Such piercing by the distal legs 337 may fix or at least partially secure the electrode 334 within the first portion 340 of paddle body.

Figure 3C:
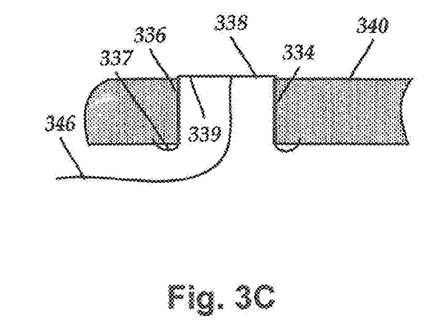
FIG. 3C is a schematic cross-section view of the embodiment of FIG. 3B in which the base has been removed and a conductor has been attached to a surface of the electrode, according to the invention.

After inserting all of the electrodes into the first portion of the paddle body, the base is then removed and conductors 346 are attached to the electrodes 334. The conductor may be attached to any suitable portion of the electrode. In at least some embodiments, a segment of the first portion 340 of the paddle body under the stimulating portion 338 of the electrode 334 is removed to create a cavity to allow access to the back surface 339 of the stimulating portion 338 of the electrode for attachment of the conductor 346. This segment of the first portion 340 of the paddle body may be removed using any suitable method including, for example, laser or mechanical cutting. Alternatively, the conductor 346 may be attached to a leg 336 of the electrode 334.

Figure 3D:
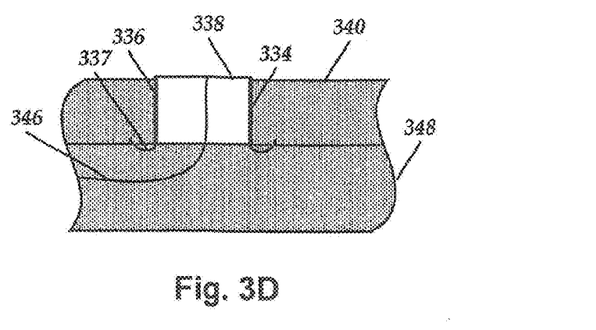
FIG. 3D is a schematic cross-section view of the embodiment of FIG. 3C in which a second portion of the paddle body has been formed, according to the invention.

The first portion 340 of the paddle body and the electrodes 334 are then placed into a mold (not shown) and a second portion 348 of the paddle body is molded over the back surface, and optionally around the sides, of the first portion 340 of the paddle body, as illustrated in FIG. 3D. In at least some embodiments, the first portion 340 and the second portion 348 of the paddle body may be further attached using an adhesive or other binder. Alternatively or additionally, the first and second portions may be reflowed to allow mingling of the material of these portions to facilitate bonding. The second portion 348 of the paddle body leaves the stimulating surfaces 338 of the electrodes 334 exposed and preferably is formed around the conductors 346. In at least some embodiments, the second portion 348 may also fill in the region of the first portion 340 that was removed for attached of the conductor 346 to the electrode 334.

Figure 4A:
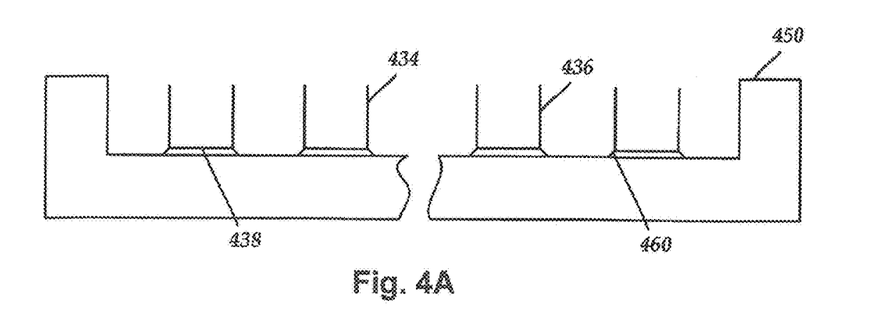
FIG. 4A is a schematic cross-sectional view of one embodiment of electrodes with sacrificial portions and legs disposed in a mold, according to the invention.

FIGS. 4A-4F illustrate another method of forming a paddle of a paddle lead using electrodes with sacrificial portions. The method includes placing electrodes 434 into a mold 450 as illustrated in FIG. 4A. Each electrode 434 includes a stimulating portion having a stimulating surface 438 to be exposed to ambient surrounding when the lead formation is complete. The electrode 434 further includes one or more leg portions 436 extending from the stimulating portion opposite to the stimulating surface 438. The stimulating surface 438 also includes one or more sacrificial portions 460 disposed on the periphery of the stimulating surface 438, optionally at an oblique angle to the stimulating surface. The sacrificial portions 460 extend from the stimulating surface 438 in a direction opposite to the leg portion 436. The sacrificial portions 460 are disposed against the surface of the mold 450 during molding of the paddle body These sacrificial portions 460 resist or prevent the flow of molding material, which is usually injected into the mold 450 as a fluid, from flowing over the stimulating surface 438 of the electrode 434. FIG. 4A is a cross-sectional view and illustrates two legs and two sacrificial portions. It will be recognized, however, that the electrode may have more than two legs or more than two sacrificial portions (or any combination thereof) distributed around the circumference of the electrode. Moreover, in some embodiments, a single leg may be provided around the circumference of the electrode with the leg portions 436 in FIG. 4A simply representing two sections of that single leg for each electrode. Furthermore, in some embodiments, a single sacrificial portion may be provided around the circumference of the electrode with the reference numeral 460 in FIG. 4A simply representing two sections of that single sacrificial portion for each electrode. In at least some embodiments, the number of legs and the number of sacrificial portions are equal. In other embodiments, the number of legs and the number of sacrificial portions are different.

Figure 4B:
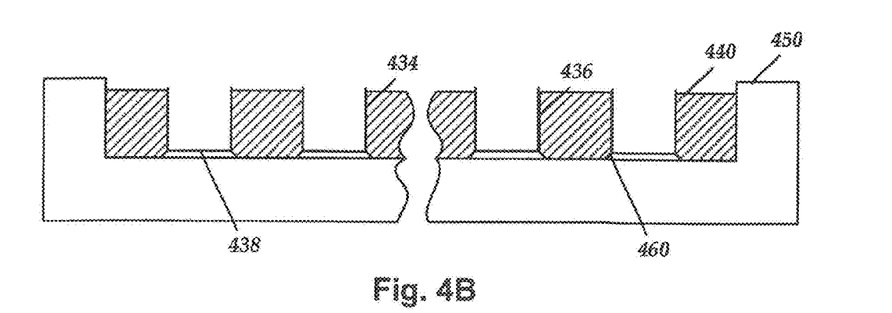
FIG. 4B is a schematic cross-section view of the embodiment of FIG. 4A in which a first portion of the paddle body has been formed between the legs of the electrodes, according to the invention.

A first portion 440 of the paddle body is formed (for example, molded) between the legs of the electrodes. Any suitable non-conductive material, including those discussed above, can be employed to mold the first portion 440 of the paddle body around the leg portions 436. In at least some embodiments, a non-conductive molding material is injected to create the first portion 440 of the paddle body for reliably securing the electrode 434 within the first portion 440 of the paddle body. In at least some embodiments, the thickness of the first portion 440 of the paddle body is less than or equal to the length of leg portions 436 of the electrodes 434.

Figure 4C:
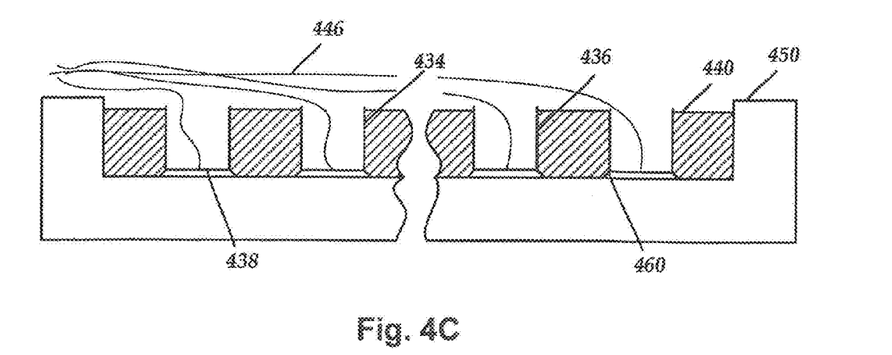
FIG. 4C is a schematic cross-section view of the embodiment of FIG. 4B in which conductor wires have been attached to the electrodes, according to the invention.
Figure 4D:
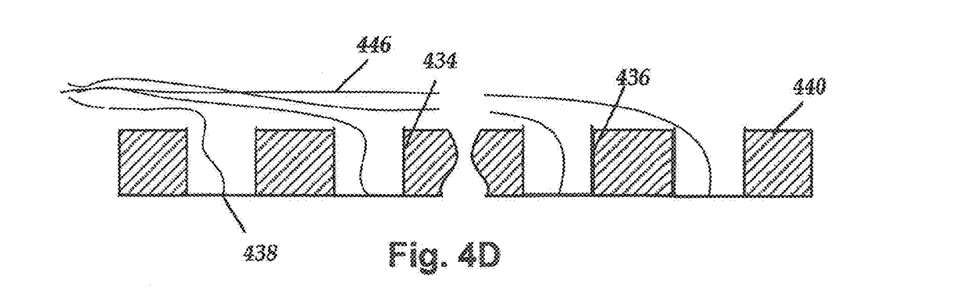
FIG. 4D is a schematic cross-section view of the embodiment of FIG. 4C in which the mold has been removed and the sacrificial portions of the electrodes have been removed, according to the invention.

A conductor wire 446 is attached to each of the electrodes 434, for example, to the surface of the electrode 4334 opposite to the stimulating surface 438 of the electrode 434, as illustrated in FIG. 4C. Subsequently, the mold 450 is removed from the arrangement of electrodes 434, conductor wires 446, and the first portion 440 of the paddle body, as illustrated in FIG. 4D. The sacrificial portions 460 of the electrodes 434 may be removed at this stage of manufacture by, for example, cutting, grinding, etching, or any other suitable technique. It will be understood that the sacrificial portions 460 may be removed later, for example, after formation of the paddle body is complete with a second portion of the lead body attached to the first portion 440 of the paddle body.

Figure 4E:
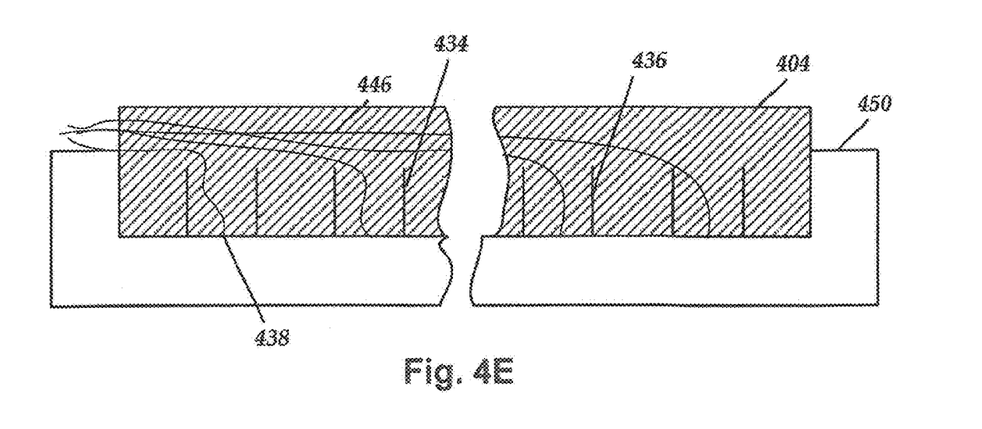
FIG. 4E is a schematic cross-section view of the embodiment of FIG. 4D in which a second portion of the paddle body has been added to form the full paddle body, according to the invention.
Figure 4F:
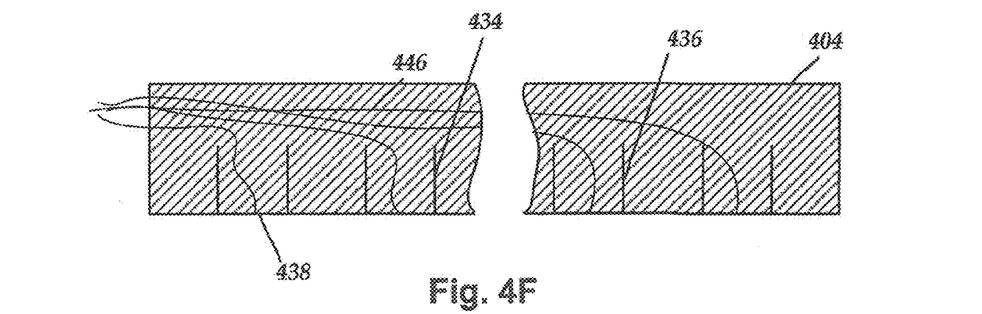
FIG. 4F is a schematic cross-section view of the embodiment of FIG. 4E in which the paddle body has been removed from the mold, according to the invention.

A second portion of the paddle body has been added to the first portion to form the full paddle body 404, as illustrated in FIG. 4E. The first portion 440 of the paddle body, which is included in the initial electrode arrangement, may be placed within a mold (the bottom part 450 of which is illustrated in FIG. 4E) and a non-conductive material may be into the mold 450 through mold ports (not shown). The non-conductive material is injected over the electrodes 434 from the side proximate to the leg portion 436 such that the non-conductive material seals the initial electrode arrangement and cures to mold the second portion of the paddle body over the first portion 440 of the paddle body. This second portion of the paddle body is molded leaving the stimulating surface 438 of the electrodes 434 exposed while covering the leg portion 436 of the electrode 434 as well as the conductor wires 446 attached to the electrodes 434. Optionally, the second portion of the paddle body may be firmly secured with the first portion 440 of the paddle body by using an adhesive or by reflowing the first and second portions of the paddle body. Once the electrodes 434, conductor wires 446, and the complete paddle body 404 are combined to create a final electrode arrangement, it is then removed from the mold 45, as illustrated shown in FIG. 4F.

Figure 5A:
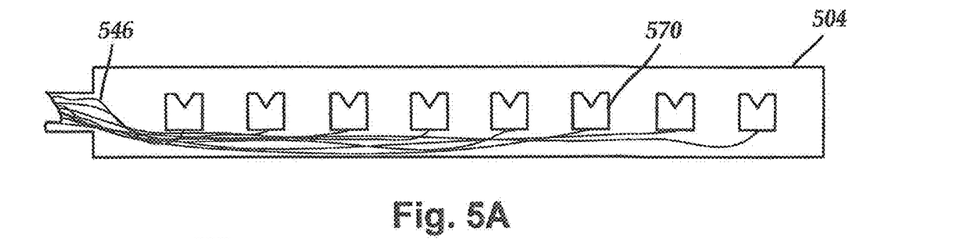
FIG. 5A is a schematic cross-sectional view of one embodiment of a paddle body with fixation elements disposed therein, according to the invention.
Figure 5B:
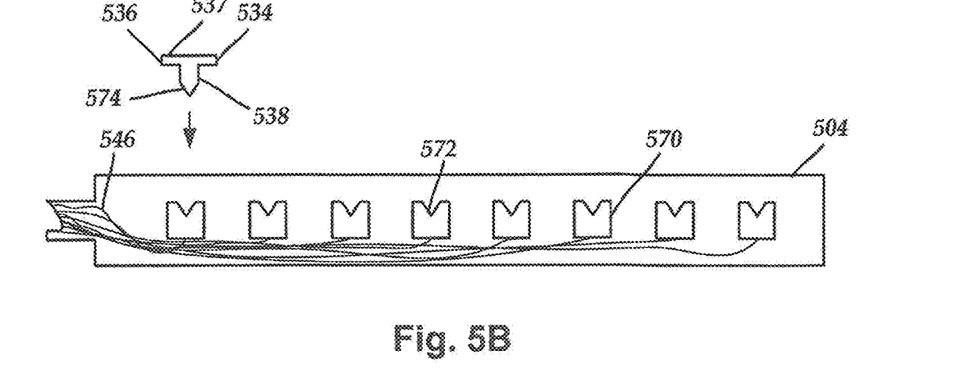
FIG. 5B is a schematic cross-section view of the embodiment of FIG. 5A in which an electrode is to be pressed into the paddle body, according to the invention.
Figure 5C:
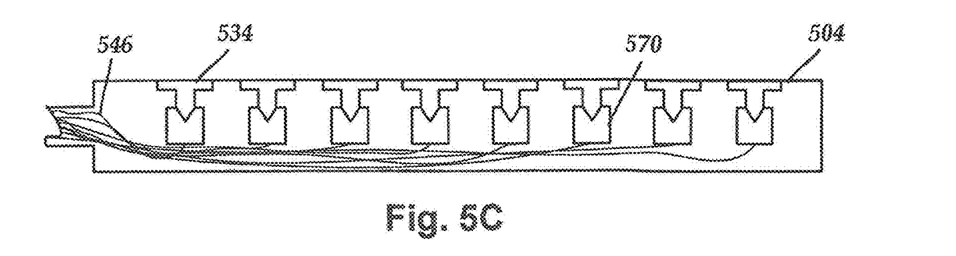
FIG. 5C is a schematic cross-section view of the embodiment of FIG. 5B in which all of the electrodes have been pressed into the paddle body and in contact with the fixation elements, according to the invention.

FIGS. 5A-5C illustrate another method of forming a paddle of a paddle lead using electrodes and embedded fixation elements. In this embodiment, the paddle body 504 may have one or more fixation elements 570 disposed, embedded, or encapsulated within the paddle body 504, as illustrated in FIG. 5A. Each fixation element 570 is physically and electrically attached to one or more conductor wires 546. In at least some embodiments, the fixation elements 570 and conductor wires 546 are molded into the paddle body 504.

Each of the fixation elements 570 are designed to receive a couple to an electrode 534. The electrode 534 includes a stimulating element 536 with an exposed stimulating surface 537, and a piercing element 538 extending from the stimulating element 536. The piercing element 538 preferably includes a sharpened distal tip 574. The piercing element 538 of the electrode 534 is pressed or otherwise inserted into the paddle body 504 to make contact with a fixation element 570, as illustrated in FIGS. 5B and 5C.

Each of the electrodes 534 may include first locking arrangement at the tip or interface 574 and each of the fixation elements may include a second locking arrangement or interface 572 such that the electrodes 534 may be secured with the fixation elements 570 when engaged with each other. As an example, the first locking arrangement 574 includes one or more ridges and the second locking arrangement 572 includes one or more detents (or vice versa) designed to receive the ridge(s). As a second example, the first locking arrangement 574 includes one or more locking ridges and the second locking arrangement 572 includes one or more spring elements (or vice versa) that allow the ridge(s) to pass over the spring element(s) during insertion, but hinder or prevent pulling the ridge(s) back over the spring element(s). In a third example, the first locking arrangement 574 includes a thread and the second locking arrangement 572 includes a corresponding groove (or vice versa) to receive the thread. In some embodiments, the first locking arrangement 574 and the second locking arrangement 572 are configured to create a snap-fit system. In a fourth example, the first locking arrangement 574 includes a ball and the second locking arrangement 572 includes a socket (or vice versa) to receive and hold the ball in place. In a fifth example, the first locking arrangement 574 includes a cantilever and the second locking arrangement 572 includes a recess (or vice versa) to receive the cantilever and hold it in place. Alternatively or additionally, each the piercing element 538 of the electrode 534 and a corresponding portion of the fixation element 570 form a friction fit when engaged with each other to maintain a contact between the electrode 534 and the fixation element 570.

Figure 5D:
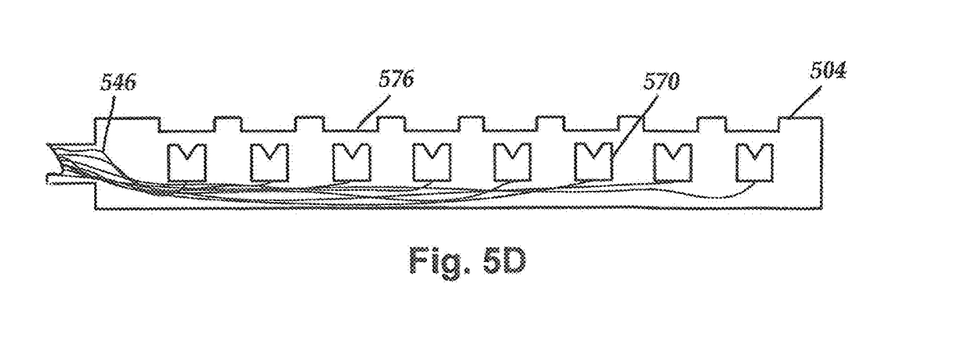
FIG. 5D is a schematic cross-section view of the another embodiment of a paddle body with fixation elements disposed therein, according to the invention.

FIG. 5D is a schematic cross-sectional view of another embodiment of a paddle body with fixation elements where the paddle body 504 includes grooves sized to receive the electrodes 534 when pressed or otherwise inserted into the paddle body 504. The electrodes 534 may be then secured or brought in contact with the fixation elements 570, as discussed above.

Figure 6A:
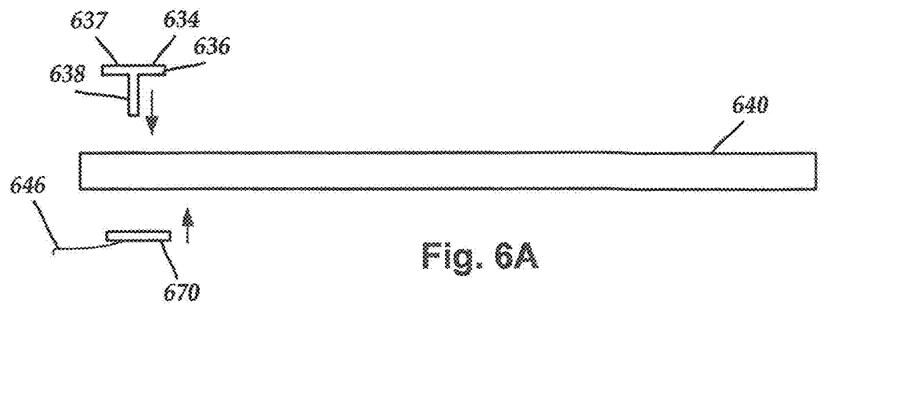
FIG. 6A is a schematic cross-sectional view of one embodiment of a first portion of a paddle body showing how an electrode and fixation element are to be brought together with the first portion of the paddle body between them, according to the invention.
Figure 6B:
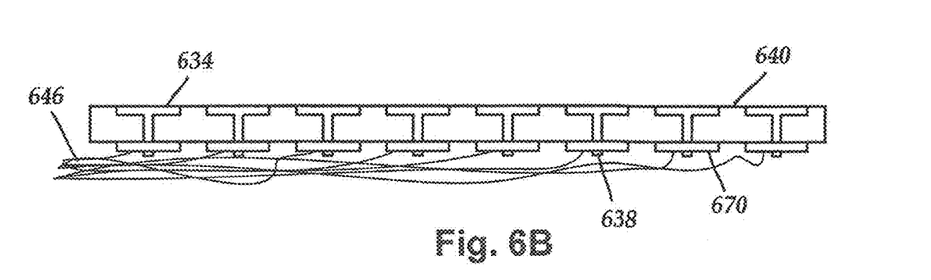
FIG. 6B is a schematic cross-section view of the embodiment of FIG. 6A in which all of the electrodes and fixation elements are coupled together with the first portion of the paddle body between, according to the invention.
Figure 6C:
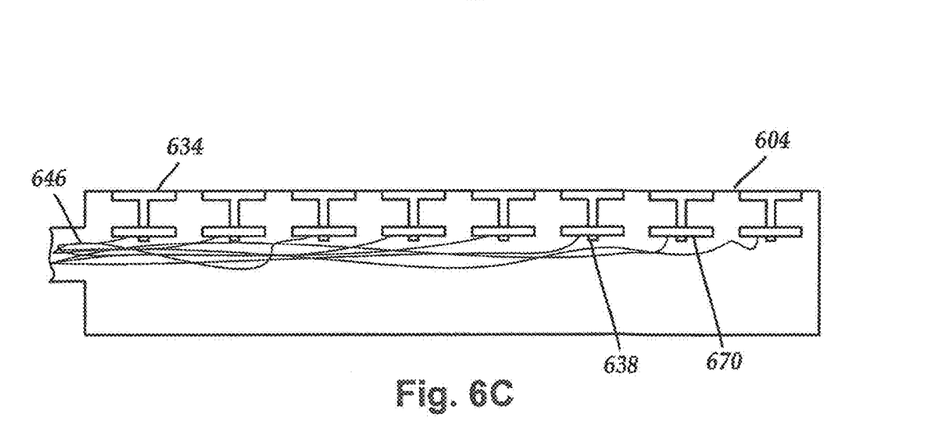
FIG. 6C is a schematic cross-section view of the embodiment of FIG. 6B in which a second portion of the paddle body has been added to form the full paddle body, according to the invention.

FIGS. 6A-6C illustrate another method of forming a paddle of a paddle lead using electrodes and fixation elements. The method includes providing a first portion 640 of a paddle body, electrode 634, and fixation elements 670 to which conductor wires 646 are, or will be, attached, as illustrated in FIG. 6A. The electrode 634 includes a stimulating element 636 having a stimulating surface 637 and a piercing element 638 extending from the stimulating element 636.

The piercing element 638 of each electrode 634 is pressed or otherwise inserted through the first portion 640 of the paddle body leaving the stimulating element 636 is disposed on the front surface of the first portion of the paddle body, as illustrated in FIG. 6B. The thickness of the first portion 640 of the paddle body should be such that the piercing element 638 extends entirely through the first portion 640 of the paddle body.

The fixation element 670 is then attached to the distal end of the piercing element of the electrode 638, as illustrated in FIG. 6B. This fixation element 670 is located on the back surface of the first portion 640 of the paddle body. Such engagement of the piercing element 638 and the fixation element 670 with the first portion 640 of the paddle body between the piercing element 638 and the fixation element 670 may secure the electrode 634 with the first portion 640 of the paddle body. The piercing element 638 and fixation element 670 may employ any of the locking arrangements described above for the embodiment illustrated in FIGS. 5A-5C. In some embodiments, the piercing element 638 may penetrate entirely through the fixation element 670. In other embodiments, the piercing element 638 does not penetrate the entire thickness of the fixation element.

Prior to or after the electrodes 634 and fixation elements 670 are coupled together with the first portion 640 of the paddle body between them, the fixation elements 670 are electrically coupled with one or more conductor wires 646. Alternatively, the conductor wires may be attached to the electrodes at, for example, the distal end of the piercing elements of the electrodes.

Subsequently, a second portion of the paddle body is molded around the fixation elements 670 and conductor wires 646 and beneath (and, optionally, around the peripheral side surface of) the first portion 640 of the paddle body to form a full paddle body 604, as illustrated in FIG. 6C. The second portion of the paddle body is formed with the stimulating surfaces 637 of the electrodes 634 remaining exposed. Optionally, the second portion of the paddle body may be firmly secured with the first portion 640 of the paddle body by using an adhesive or by reflowing the first and second portions of the paddle body.

Figure 7:
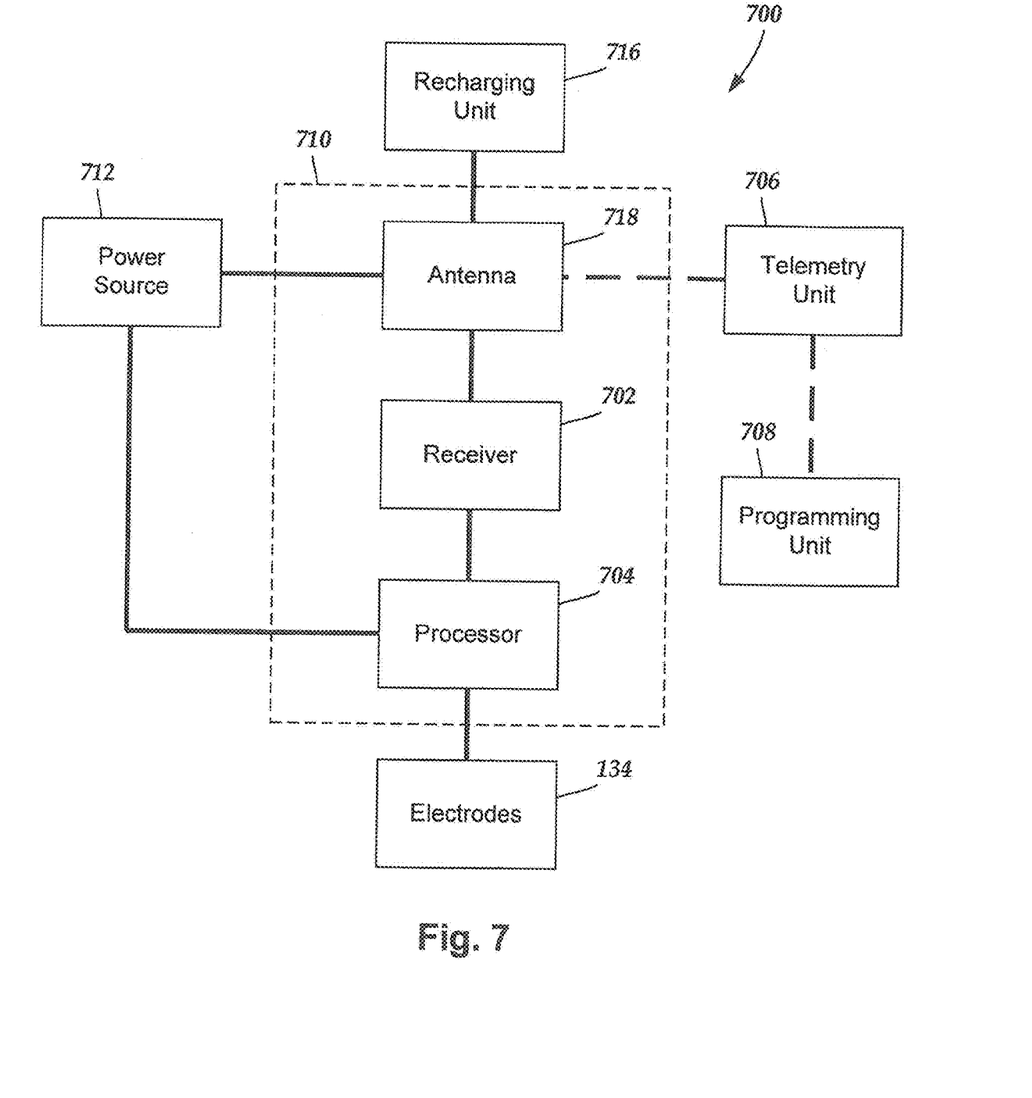
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
    a paddle body comprising a non-conductive, biocompatible material;
    at least one lead body having a distal end, a proximal end, and a longitudinal length, the distal end of each of the at least one lead bodies coupled to the paddle body;
    a plurality of electrically conductive fixation elements embedded within the paddle body so that the non-conductive material of the paddle body surrounds and is in contact with a plurality of surfaces of each of the fixation elements;
    a plurality of electrodes disposed on the paddle body, each electrode comprising a stimulating element with an exposed stimulation surface and a piercing element extending from the stimulating element into the paddle body and making contact with at least one of the plurality of fixation elements, wherein the piercing element comprises a post that engages the at least one of the fixation elements to physically and electrically couple the post to the at least one of the fixation elements;
    a plurality of terminals disposed along the proximal ends of each of the at least one lead bodies; and
    a plurality of conductor wires, each conductor wire of the plurality of conductor wires electrically coupling each of the plurality of terminals to at least one of the plurality of electrodes.

2. The electrical stimulation lead of claim 1, wherein each of the plurality of electrodes comprises a first locking arrangement and each of the plurality of fixation elements comprises a second locking arrangement and wherein the first and second locking arrangements are configured and arranged, when engaged with each other, to lock a one of the electrodes to a one of the fixation elements.

3. The electrical stimulation lead of claim 2, wherein a one of the first and second locking arrangements comprises a ridge and another one of the first and second locking arrangements comprises a detent configured and arranged to receive the ridge.

4. The electrical stimulation lead of claim 2, wherein a one of the first and second locking arrangements comprises a threading and another one of the first and second locking arrangements comprises a groove configured and arranged to receive the threading.

5. The electrical stimulation lead of claim 2, wherein a one of the first and second locking arrangements comprises a ball and another one of the first and second locking arrangements comprises a socket configured and arranged to receive the ball.

6. The electrical stimulation lead of claim 2, wherein a one of the first and second locking arrangements comprises a cantilever and another one of the first and second locking arrangements comprises a recess configured and arranged to receive the cantilever and hold the cantilever in place.

7. The electrical stimulation lead of claim 1, wherein each of the plurality of electrodes comprises a first fitting arrangement and each of the plurality of fixation elements comprises a second fitting arrangement and wherein the first and second fitting arrangements are configured and arranged, when engaged with each other, to form a friction fit between a one of the electrodes to a one of the fixation elements to facilitate maintaining contact therebetween.

8. The electrical stimulation lead of claim 1, wherein the piercing element comprises a sharpened distal tip.

9. The electrical stimulation lead of claim 1, wherein each of the conductor wires is physically attached to at least one of the plurality of fixation elements.

10. The electrical stimulation lead of claim 1 wherein the piercing element of each electrode extends into and entirely through at least one of the fixation elements.

11. A method of making the electrical stimulation lead of claim 1, the method comprising:
coupling at least one of the plurality of conductive wires to each of the plurality of fixation elements;
forming the paddle body around the plurality of fixation elements; and
pressing the piercing element of each of the plurality of electrodes into the paddle body and into electrical contact with at least one of the plurality of fixation elements.

12. A method of making the electrical stimulation lead of claim 1, the method comprising:
pressing the piercing element of each of the plurality of electrodes through a first portion of the paddle body, the first portion of the paddle body having a front surface and a back surface with the stimulation element of each of the electrodes disposed on the front surface;
attaching at least one of the plurality of fixation elements to each of the plurality of electrodes with the fixation elements disposed on the back surface of the first portion of the paddle body;
coupling at least one of the plurality of conductive wires to each of the plurality of fixation elements or electrodes; and
forming a second portion of the paddle body around the plurality of ixation elements and at least partially beneath the first portion of the paddle body.

13. The electrical stimulation lead of claim 1, each of the conductor wires is physically and electrically attached to at least one of the plurality of fixation elements.

14. The electrical stimulation lead of claim 1, each of the fixation elements is electrically coupled to at least one of the conductor wires.

15. The electrical stimulation lead of claim 1, wherein each of the fixation elements is surrounded by the lead body.

16. The electrical stimulation lead of claim 1, wherein each of the electrodes makes contact with a different one of the plurality of fixation elements.

17. The electrical stimulation lead of claim 1, each conductor wire of the plurality of conductor wires electrically coupling each of the plurality of terminals to at least one of the plurality of electrodes via a one of the plurality of fixation elements.

18. The electrical stimulation lead of claim 1, wherein the paddle body comprises a first portion and a second portion disposed on the first portion, wherein each of the fixation elements is disposed between the first and second portions of the paddle body.

19. The electrical stimulation lead of claim 18, wherein the piercing element of each of the electrodes extends through the first portion of the paddle body to make contact with a one of the fixation elements.

20. An electrical stimulation lead, comprising:
a paddle body;
at least one lead body having a distal end, a proximal end, and a longitudinal length, the distal end of each of the at least one lead bodies coupled to the paddle body;
a plurality of fixation elements disposed entirely within the paddle body;
a plurality of electrodes disposed on the paddle body, each electrode comprising a stimulating element with an exposed stimulation surface and a piercing element extending from the stimulating element into the paddle body and making contact with at least one of the plurality of fixation elements;
a plurality of terminals disposed along the proximal ends of each of the at least one lead bodies; and
a plurality of conductor wires, each conductor wire of the plurality of conductor wires electrically coupling each of the plurality of terminals to at least one of the plurality of electrodes,
wherein each of the plurality of electrodes comprises a first locking arrangement and each of the plurality of fixation elements comprises a second locking arrangement and wherein the first and second locking arrangements are configured and arranged, when engaged with each other, to lock a one of the electrodes to a one of the fixation elements, wherein a one of the first and second locking arrangements comprises a locking ridge and another one of the first and second locking arrangements comprises a spring element configured and arranged to allow the ridge to pass over the spring element and to hinder reversing passage of the ridge over the spring element.

* * * * *